United States Patent [19]
Weers et al.

[11] Patent Number: 5,635,538
[45] Date of Patent: *Jun. 3, 1997

[54] FLUOROCARBON EMULSIONS WITH REDUCED PULMONARY GAS-TRAPPING PROPERTIES

[75] Inventors: Jeffry G. Weers; Ernest G. Schutt; Timothy J. Pelura; Peter E. Keipert, all of San Diego, Calif.

[73] Assignee: Alliance Pharmaceutical Corp., San Diego, Calif.

[*] Notice: The term of this patent shall not extend beyond the expiration date of Pat. No. 5,608,930.

[21] Appl. No.: 32,333

[22] Filed: Mar. 16, 1993

[51] Int. Cl.$^6$ .............................. A61K 31/02; B01J 13/00
[52] U.S. Cl. .................. 514/743; 252/312; 252/314; 514/757; 514/761; 514/832; 514/833
[58] Field of Search .................................. 514/743, 744, 514/746, 759, 761, 832, 833, 757; 252/312, 314

[56] References Cited

U.S. PATENT DOCUMENTS

| | | | |
|---|---|---|---|
| 3,975,512 | 8/1976 | Long | 252/312 |
| 4,613,708 | 9/1986 | Riess et al. | 514/832 X |
| 4,640,833 | 2/1987 | Tamborski et al. | 424/5 |
| 4,859,363 | 8/1989 | Davis et al. | 252/312 |
| 4,865,836 | 9/1989 | Long, Jr. | 514/832 |
| 4,866,096 | 9/1989 | Schweighardt | 514/747 |
| 4,895,876 | 1/1990 | Schweighardt et al. | 514/747 |
| 4,987,154 | 1/1991 | Long, Jr. | 514/832 |
| 5,120,731 | 6/1992 | Meinert et al. | 514/231.5 |
| 5,264,220 | 11/1993 | Long, Jr. et al. | 514/832 X |
| 5,393,513 | 2/1995 | Long, Jr. | 514/757 |

FOREIGN PATENT DOCUMENTS

| | | |
|---|---|---|
| 0051526 | 10/1981 | European Pat. Off. . |
| WO 91/00110 | 1/1991 | WIPO . |
| WO9301798 | 7/1992 | WIPO . |

OTHER PUBLICATIONS

Lawson et al., "Methods for the Estimation of Vapor Pressures and Oxygen Solubilities of Fluorochemicals for Possible Application in Artificial Blood Formulations", *Journal of Fuorine Chemistry*, 12(1978) pp. 221–236.

Clark, et al. "Response of the Rabbit Lung as a Criterion of Safety for Fluorocarbon Breathing and Blood Substitutes" Biomat. Art. Cells & Immob. Biotech. 20(2–4): 1085–1099 (1992). (month unknown).

Geyer, R. "Whole Animal Perfusion with Fluorocarbon Dispersions" Federation Procedures 29(5): 1758–1763 (1970).

Kabal'nov, et al. "Influence of Nature and Composition od Disperse Phase in Emulsions of Perfluoroorganic Compounds on the Kinetics of the Decrease in Emulsion Dispersity" Kolloidnyi Zhurnal 48(1): 20–24 (1986).

Riess, J. "Reassessment of Criteria for the Selection of Perfluorochemicals for Second–Generation Blood Substitutes: Analysis of Structure/Property Relationships" Artificial Organs 8(1): 44–56 (1984).

Riess, et al. "Post–Fluosol Progress in Fluorocarbon Emulsions for in vivo Oxygen Delivery" *International Symposium on Artificial Blood Substitutes*, Bari. Italy, 135–166 (1987).

*Primary Examiner*—Richard D. Lovering
*Assistant Examiner*—Daniel S. Metzmaier
*Attorney, Agent, or Firm*—Knobbe, Martens, Olson & Bear

[57] ABSTRACT

A fluorocarbon emulsion which exhibits reduced pulmonary gas-trapping properties in species-sensitive laboratory animals is disclosed. Additionally, the fluorocarbon component (s) exhibit short organ retention time(s). The emulsion includes an aqueous phase, an emulsifier, and a fluorocarbon (or fluorocarbon composition), having a vapor pressure of less than about 8 torr to reduce pulmonary gas-trapping, and having an organ retention half life of less than about 6 weeks and more preferably less than about 3 to 4 weeks.

15 Claims, 7 Drawing Sheets

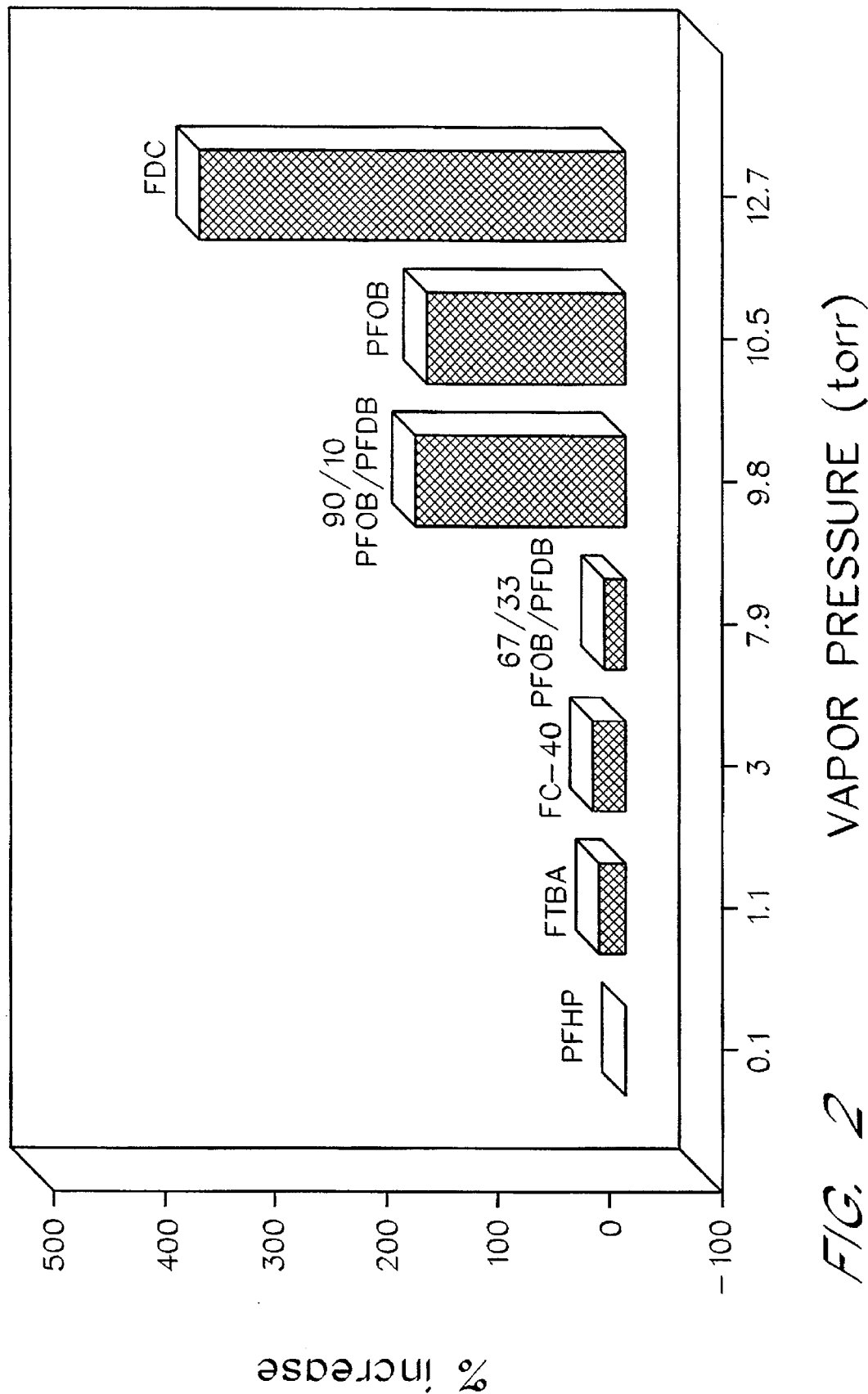

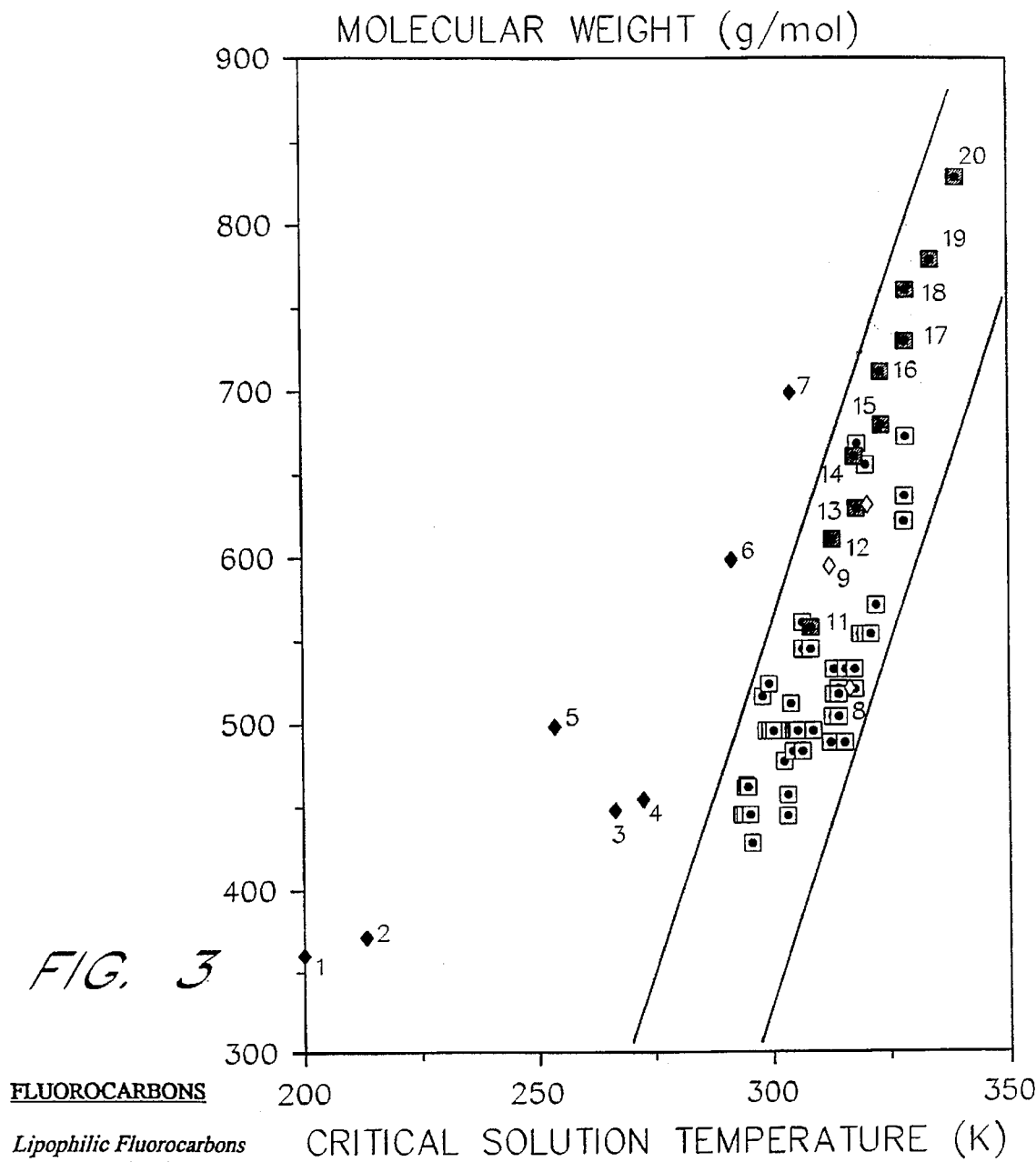

FIG. 3

FLUOROCARBONS

*Lipophilic Fluorocarbons*
1. Br $C_4F_8$Br
2. $ClC_6F_{12}Cl$
3. $C_8F_{17}C_2H_5$
4. $C_8F_{17}Cl$
5. $C_8F_{17}Br$
6. $C_{10}F_{21}Br$ (F-decyl bromide)
7. $C_{11}F_{23}O_3Br$

*Green Cross - Fluosol*
8. $(C_3F_7)_3N$ (F-tripropylamine)

*Perftoran (Kabalnov et al.; Kolloidn Zh. 48: 27-32 (1986))*
9. $C_{12}F_{23}N$ (F-methylcyclohexylpiperidine)

*Davis (U.S. Patent No. 4,859,363)*
10. $C_{14}F_{24}$ (F-perhydrophenanthrene)

*Meinert (U.S. Patent No. 5,120,731)*
11. $C_{10}F_{20}O_2N_2$ (F-dimorpholinoethane)
12. $C_{11}F_{22}O_2N_2$ (F-dimorphalinopropane)
13. $C_{12}F_{24}N_2$ (F-dipiperidinoethane)
14. $C_{12}F_{24}O_2N_2$ (F-dimorpholinobutane)
15. $C_{13}F_{26}N_2$ (F-dipiperidinopropane)
16. $C_{13}F_{26}O_2N_2$ (F-dimorphalinopentane)
17. $C_{14}F_{28}N_2$ (F-dipiperidinobutane)
18. $C_{14}F_{28}O_2N_2$ (F-dimorpholinohexane)
19. $C_{15}F_{30}N_2$ (F-dipiperidinopentane)
20. $C_{16}F_{32}N_2$ (F-dipiperidinohexane)

*50 Other Fluorocarbons- open squares*
*(Yamanouchi et al.; Chem. Pharm. Bull. 33: 1221 (1985))*

ALTERNATIVE FLUOROCARBONS TO PREVENT PGT

| CHEMICAL STRUCTURE | MW (g/mol) | BP (°C) | $P_v^{37}$ (torr) | $t_{1/2}$ (days) | mp (°C) |
|---|---|---|---|---|---|
| $CF_3(CF_2)_8Br$ | 549 | 160.5 | 5.2 | 7.0 | 29 |
| $(CF_3)_2CF(CF_2)_3CF(CF_3)CF_2Br$ | 549 | 155 | 6 | 7.0 | <−50 |
| $CF_3(CF_2)_9Br$ | 599 | 198 | 1.5 | 19.7 | 55 |
| $CF_3(CF_2)_7C_2H_5$ | 448 | 160 | 6 | 6 | <20 |
| $(CF_3)_2CFO(CF_2)_8Br$ | 665 | 188 | 4 | 15 | 0 |
| $C_2F_5CF(CF_3)O(CF_2)_6Br$ | 615 | 171 | 7 | 9 | −12 |
| $CF_3(CF_2)_7O(CF_3)_2Br$ | 615 | 171 | 7 | 9 | −12 |
| $CF_3(CF_2)_7OCF(CF_3)CF_2Br$ | 665 | 188 | 4 | 15 | 0 |
| $F(CF(CF_3)OCF_2O)_2CF_2CF_2Br$ | 697 | 190 | 3 | 16 | −90 |
| $F(CF(CF_3)CF_2O)_2CF(CF_3)CF_2Br$ | 581 | 166 | 6 | 8 | −95 |
| $BrCF_2(CF_2)Br$ | 560 | 172 | 4 | 7 | 35 |
| $BrCF_2(CF_2)_6Br$ | 510 | 155 | 6 | 5 | 15 |
| $Br(CF_2CF_2O)_3CF_2CF_2Br$ | 608 | — | — | — | — |

Most of the values presented in the Table above were calculated from Hildebrand solubility theory by Yong Ni and Dian Song (Alliance Pharmaceutical Corp. Project Report; "Perfluorochemicals with Low Vapor Pressure — I. Key Properties and Synthesis of Candidate PFCc"; dated 9/14/92.

FIG. 7

FLUOROCARBON EMULSIONS WITH REDUCED PULMONARY GAS-TRAPPING PROPERTIES

BACKGROUND OF THE INVENTION

The present invention relates to emulsions comprising highly fluorinated or perfluorinated compounds. More particularly, it relates to fluorocarbon emulsions exhibiting reduced pulmonary gas-trapping properties.

Fluorocarbon emulsions find uses as therapeutic and diagnostic agents. Most therapeutic uses of fluorocarbons are related to the remarkable oxygen-carrying capacity of these compounds. One commercial biomedical fluorocarbon emulsion, Fluosol (Green Cross Corp., Osaka, Japan), is presently used as an oxygen carrier to enhance oxygen delivery to the myocardium during percutaneous transluminal coronary angioplasty (Fluosol, Summary Basis of Approval, Reference No. OB-NDA86-0909, December 1989). Fluorocarbon emulsions have also been used in diagnostic applications such as imaging. Radiopaque fluorocarbons such as perflubron (perfluorooctyl bromide or $C_8F_{17}Br$) are particularly useful for this purpose.

Increased pulmonary residual volume (IPRV) has been observed in association with the intravenous administration of various perfluorocarbon emulsions in certain animal species. While the direct correlation between IPRV and pulmonary dysfunction has not been positively identified, dysfunction (including reduced arterial $PO_2$, signs of respiratory distress, and even lethality) has been observed on occasions in certain sensitive animal species in which IPRV was later identified.

IPRV occurs as a result of gas-trapping within the pulmonary system, and prevents the normal deflation of lungs when intrathoracic pressure is equalized to ambient pressure such as during necropsy of an animal. It is believed that gas-trapping occurs as a consequence of foam or bubble formation in the lungs. It is noted that under normal circumstances, bubbles or liquid bridges form and disappear spontaneously within alveoli without a gas-trapping effect. It is believed, however, that IPRV occurs when these bubbles grow in the presence of fluorocarbon vapors, trapping larger amounts of air within the lung. As stated above, if bubble formation continues, pulmonary dysfunction can result (in certain animal species). IPRV depends on the vapor pressure of the fluorocarbon component(s), with lower vapor pressure fluorocarbons not exhibiting the phenomenon. Diminution of the vapor pressure of the fluorocarbon component(s) also plays a critical role in stabilizing the emulsion droplets against Ostwald ripening, the key destabilizing mechanism at work in small particle fluorocarbon emulsions. The prior art has described fluorocarbon emulsion formulations designed to inhibit Ostwald ripening. See, e.g. Davis et al., U.S. Pat. No. 4,859,363; Meinert, U.S. Pat. No. 5,120,731; Kabalnov et al., Kolloidn Zh., 48: 27–32 (1986). These formulations contain a mixture of two fluorocarbon components, the secondary fluorocarbon component having a significantly higher molecular weight, and lower vapor pressure relative to the primary fluorocarbon component.

Following intravenous administration, fluorocarbon emulsion particles are taken up and temporarily retained by cells of the reticuloendothelial system (RES). It is desirable to minimize this retention time (all references to organ half-life or organ retention which follow refer specifically to retention in the RES organs, principally liver and spleen). Unfortunately, when the prior art included higher molecular weight fluorocarbons in fluorocarbon emulsions, organ retention times were also increased considerably. Organ retention times for most fluorocarbons bear an exponential relationship to the molecular weight of the fluorocarbon and are critically dependent on dose and animal species. See J. G. Riess, Artificial Organs 8: 44, 49–51 (1984); J. G. Riess, International Symposium on Blood Substitutes, Bari, Italy: Jun. 19–20, 1987, Proceedings pp. 135–166.

There is a need for perfluorocarbon emulsions that do not exhibit, or exhibit reduced pulmonary gas-trapping properties, and also have a short organ retention time. Accordingly, it is an object of the invention to provide fluorocarbon emulsions having these characteristics.

SUMMARY OF THE INVENTION

The present invention involves fluorocarbon emulsions which unexpectedly exhibit both reduced pulmonary gas-trapping properties, and a short RES organ retention time.

Thus, in accordance with the present invention, there is provided a fluorocarbon emulsion which has the following properties: (1) the fluorocarbon component(s) has (have) a vapor pressure at 37 degrees celsius of less than 20 torr, preferably less than 10 torr, and most preferably less than 8 torr, in order to preclude pulmonary gas-trapping; and (2) the fluorocarbon component(s) has (have) organ half-lives significantly less than would be predicted for their molecular weight, preferably less than about 6 weeks, and more preferably less than about 3 to 4 weeks.

In one preferred embodiment, the emulsion comprises an aqueous phase, an emulsifying agent, and a single low vapor pressure, lipophilic fluorocarbon. It has been determined that there are few fluorocarbons presently known which exhibit the above stated characteristics. Several fluorocarbons which appear suitable as a single fluorocarbon with a lipophilic moiety to eliminate IPRV are listed in FIG. 7, and include: $CF_3(CF_2)_8Br$, $(CF_3)_2CF(CF_2)_3CF(CF_3)CF_2Br$, F-octyl ethane and F-bromoethers.

In another preferred embodiment, the fluorocarbon is a mixture of two or more fluorocarbons (the "fluorocarbon phase"). The emulsion may contain a fluorocarbon composition where the fluorocarbon phase comprises from about 50% to about 99.9% w/w of a first fluorocarbon, and from about 0.1% to about 50% w/w of a second fluorocarbon having a vapor pressure less than the first fluorocarbon, and which includes at least one lipophilic moiety. In particular, in the second fluorocarbon, the lipophilic moiety or moieties are advantageously Br, Cl, I, H, $CH_3$, or a saturated or unsaturated hydrocarbon chain of 2 or 3 carbon atoms. In one preferred embodiment, the second fluorocarbon is an aliphatic perfluorocarbon having the general formula $C_nF_{2n+1}R$ or $C_nF_{2n}R_2$, wherein n is an integer from 9 to 12 and R is the lipophilic moiety. In various preferred embodiments, the second fluorocarbon is selected from the group consisting of perfluorodecyl bromide, $C_{10}F_{21}CH{=}CH_2$, or $C_{10}F_{21}CH_2CH_3$, or linear or branched brominated perfluorinated alkyl ethers. Most preferably, the second fluorocarbon comprises perfluorodecyl bromide. It is desirable that each second fluorocarbon has a molecular weight greater than about 550 Daltons. Pursuant to an alternative definition of the second fluorocarbon, each second fluorocarbon has a critical solution temperature in hexane at least 10° C. lower than that of a fully fluorinated fluorocarbon having substantially the same molecular weight (i.e., a molecular weight within 10, and preferably within 3, 4, or 5 daltons). In preferred emulsions, the discontinuous fluorocarbon phase comprises from about 60% to about 99.5% w/w of the first fluorocarbon, and from about 0.5% to about 40% w/w of the second fluorocarbon; more preferably from about 60% to about 80% w/w of the first fluorocarbon, and from about 20% to about 40% w/w of the second fluorocarbon. The first fluorocarbon component in these mixtures has a molecular weight from about 460 to 550 Daltons, and has a half-life in the organs of less than about 4 weeks, more preferably less than about 2 or 3 weeks, and most preferably 7 days or less. In particular, the fluorocarbon phase preferably comprises a suitable mixture of perfluorooctyl bromide (PFOB, USAN perflubron) and perfluorodecyl bromide (PFDB).

Focusing specifically on particular embodiments, one aspect of the present invention is a fluorocarbon emulsion exhibiting reduced pulmonary gas-trapping properties, comprising an aqueous phase, an emulsifying agent, and a liquid fluorocarbon phase having a vapor pressure of less than about 20 torr at 37° C., having an organ half-life of less than about 6 weeks, and having a fluorocarbon with a lipophilic moiety, the fluorocarbon phase comprising a mixture of at least two fluorocarbons in a weight ratio of from about 20:1 to about 1:20. Preferably, the fluorocarbon phase comprises a first fluorocarbon having an organ half-life of less than about 4 weeks, and a second fluorocarbon having a vapor pressure less than the first fluorocarbon. In one embodiment, the first fluorocarbon has a molecular weight of about 460 to 550 Daltons, and the second fluorocarbon has a molecular weight of about 560 to 700 Daltons. In another embodiment, the fluorocarbon phase has a vapor pressure at 37° C. of less than about 10 torr, preferably less than about 8 torr.

In another embodiment, the invention is a fluorocarbon emulsion exhibiting reduced pulmonary gas-trapping properties, comprising an aqueous phase, an emulsifier, and a fluorocarbon phase including at least 10% weight by volume of F-decyl bromide. In this emulsion, the fluorocarbon phase may advantageously additionally comprise F-octyl bromide, and the F-octyl bromide is preferably present in the fluorocarbon phase at about 45% to 80% or 90% weight per volume, and the F-decyl bromide is present in the fluorocarbon phase at about 10 to 55% weight per volume.

Still another embodiment of the present invention is a fluorocarbon emulsion exhibiting reduced pulmonary gas trapping, comprising an aqueous phase, an emulsifier, and a fluorocarbon phase consisting essentially of a single low vapor pressure, lipophilic fluorocarbon having an organ half-life of less than about 6 weeks, and a vapor pressure at 37° C. of less than 10 torr. Suitable fluorocarbons for the fluorocarbon phase are F-octyl ethane and F-decyl ethane. Preferably, the fluorocarbon has an organ half-life of less than 3 to 4 weeks. In a preferred embodiment, the fluorocarbon has a vapor pressure at 37° C. of less than 8 torr.

In another embodiment, the invention is a method of preparing a fluorocarbon emulsion for intravenous administration to a patient, by forming an emulsion of an aqueous phase, an emulsifier, and a first fluorocarbon in a fluorocarbon phase wherein the vapor pressure of the fluorocarbon phase is greater than about 8 torr at 37° C., the improvement comprising reducing the pulmonary gas trapping effect of the emulsion upon intravenous administration by providing in combination with the first fluorocarbon in the fluorocarbon phase an effective amount of a second fluorocarbon, wherein the addition of the second fluorocarbon reduces the vapor pressure of the fluorocarbon phase at 37° C. to less than about 8 torr, wherein the fluorocarbon phase has a melting point less than about 37° C. and an organ retention half-life less than about 4 weeks. As above, the second fluorocarbon preferably includes a lipophilic moiety, and more preferably is a bromofluorocarbon.

Finally, the invention includes a method for administering a fluorocarbon emulsion to a mammal, wherein the emulsion comprises an aqueous phase, an emulsifier, and a first fluorocarbon in a fluorocarbon phase wherein the vapor pressure of the fluorocarbon phase is greater than about 8 torr at 37° C., and wherein the improvement comprises reducing the pulmonary gas trapping effect of the emulsion upon intravenous administration by providing in combination with the first fluorocarbon in the fluorocarbon phase an effective amount of a second fluorocarbon, wherein the addition of the second fluorocarbon reduces the vapor pressure of the fluorocarbon phase at 37° C. to less than about 8 torr, wherein the fluorocarbon phase has a melting point less than about 37° C. and an organ retention half-life less than about 4 weeks.

As noted, one of the criteria for the emulsions of this invention is that the fluorocarbon component(s) exhibit a short organ retention time. One low vapor pressure lipophilic fluorocarbon, perfluorodecyl bromide, for example, has a RES half life in vivo of approximately 23 days, while those of nonlipophilic perfluorocarbons having about the same molecular weight vary from about 60 to 300 days (See Table I). This distinction is critical; it spells the difference between formulations which are physiologically acceptable and those which are not. Note that none of the prior art low vapor pressure fluorocarbons are lipophilic; thus, none share the advantageous properties of the present invention. For example, with reference to Table I and FIG. 3, the fluorocarbons of the present invention all have critical solution temperatures (CSTs) and projected organ retention times much lower than those of the prior art fluorocarbons of Davis, et al., Kabalnov, and Meinert. Aside from the fluorocarbons of the present invention, conventional fluorocarbons exhibit a direct correlation between retention time in RES organs and molecular weight. Also, aside from the lipophilic fluorocarbons used in the present invention, the perfluorochemical structure has little effect on the strong retention time/molecular weight relationship. Thus, the presence of heteroatoms or cyclic structure has little effect on organ retention time.

A particularly preferred emulsifier for use in the present invention is egg yolk phospholipid, and preferred amounts of this emulsifier are 1%–10% w/v. Also preferred are the fluorinated surfactants.

BRIEF DESCRIPTION OF THE DRAWINGS

FIG. 2 is a graph which illustrates the increase in lung volume which occurs in rabbits as a result of pulmonary gas trapping following intravenous administration at a dose of 5.4 g PFC/kg. The formulations tested are concentrated (90% w/v) fluorocarbon emulsions stabilized by 4% egg yolk phospholipid.

FIG. 3 represents a plot of fluorocarbon molecular weight (g/mol) versus critical solution temperature in hexane (°K.) for various fluorocarbons including the prior art emulsion stabilizers proposed by Davis, Meinert, and Kabalnov.

FIG. 7 is a table listing various properties of fluorocarbons.

DESCRIPTION OF THE PREFERRED EMBODIMENTS

I. Introduction

The fluorocarbon emulsions of the present invention comprise two phases: a continuous aqueous phase and a discontinuous fluorocarbon phase. Osmotic agents and buffers, generally, are also included in the continuous phase to maintain osmolality and pH to promote physiological acceptability.

The discontinuous phase of modern fluorocarbon emulsions for therapeutic use generally comprises from 20% w/v to up to 125% w/v of a fluorocarbon or a highly fluorinated compound (hereinafter referred as a "fluorocarbon" or a "perfluorocarbon"). As used herein, the expression "weight per volume" or "w/v" will mean grams per 100 cubic centimeters or milliliters.

The present invention provides a fluorocarbon emulsion which exhibits reduced pulmonary gas-trapping properties, and which has a short organ retention time.

In the first instance, in order to reduce pulmonary gas-trapping, it is desired that the fluorocarbon emulsion include a fluorocarbon, or mixture thereof, which has a vapor pressure of less than 20 torr, and most preferably less than 8 torr.

Further, in order to prevent long body retention time, it is desired that the single fluorocarbon be lipophilic. Alternatively, as stated above, the emulsion may comprise a mixture of fluorocarbons in which a second fluorocarbon is added to a first, the second fluorocarbon having a relatively higher molecular weight and lower vapor pressure, and includes in its molecular structure a lipophilic moiety. In such form, emulsions of the present invention will exhibit reduced IPRV.

II. The Compositions

A. The Fluorocarbon

The characteristics of fluorocarbons suitable for use in the present invention are discussed in more detail below. Examples of suitable fluorocarbons are provided.

1. The fluorocarbon which is to be administered in emulsion form is chosen in order to prevent or reduce pulmonary gas-trapping. It has previously been found that intravascular administration of fluorocarbon emulsions having vapor pressures of around 30 torr cause gas/vapor microbubble intravascular embolism. In order to prevent this effect, it is desired that the fluorocarbon have, in the first instance, a vapor pressure of less than about 20 torr.

Figure 1:
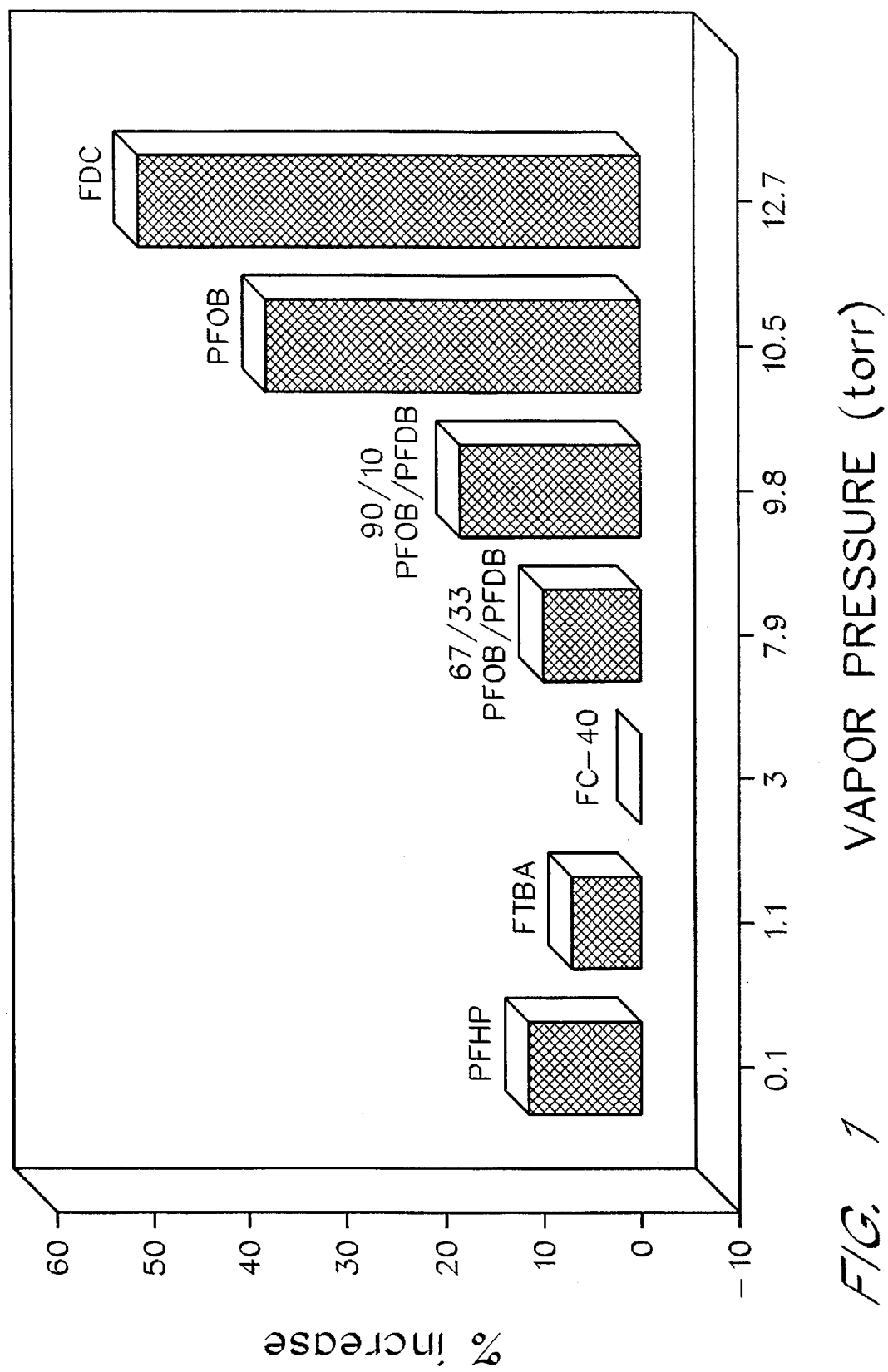
FIG. 1 is a graph which illustrates the increase in lung volume which occurs in rats as a result of pulmonary gas trapping following intravenous administration at a dose of 5.4 g PFC/kg. The formulations tested are concentrated (90% w/v) fluorocarbon emulsions stabilized by 4% egg yolk phospholipid.

Referring to FIGS. 1 and 2, the effect of vapor pressure of the administered fluorocarbon upon pulmonary gas-trapping (PGT) is illustrated in rats and rabbits. As is clearly seen, there is an increase in PGT once the vapor pressure of the fluorocarbon exceeds approximately 8 torr. At intermediate vapor pressure levels, such as 12–13 torr, it has been found that gas/vapor intravascular emboli does not occur, however, a larger degree of increased pulmonary residual volume (IPRV) occurs. It is therefore desired that any fluorocarbon used in such a fluorocarbon emulsion have a vapor pressure of less than about 20, and it is preferred that the vapor pressure be less than 15, 14, or 13 torr, and more preferedly that the vapor pressure be less than about 12, 11, or 10 torr, and most preferedly that the vapor pressure be less than 9, 8, or 7 torr.

As stated above, however, vapor pressure as related to IPRV is not the sole criteria for selecting the fluorocarbon. In particular, it is desired that the fluorocarbon have a short body retention time. Preferably, the half-life of the fluorocarbon in organs is less than 6 weeks, and most preferedly that the half-life is less than 3 to 4 weeks.

Figure 4:
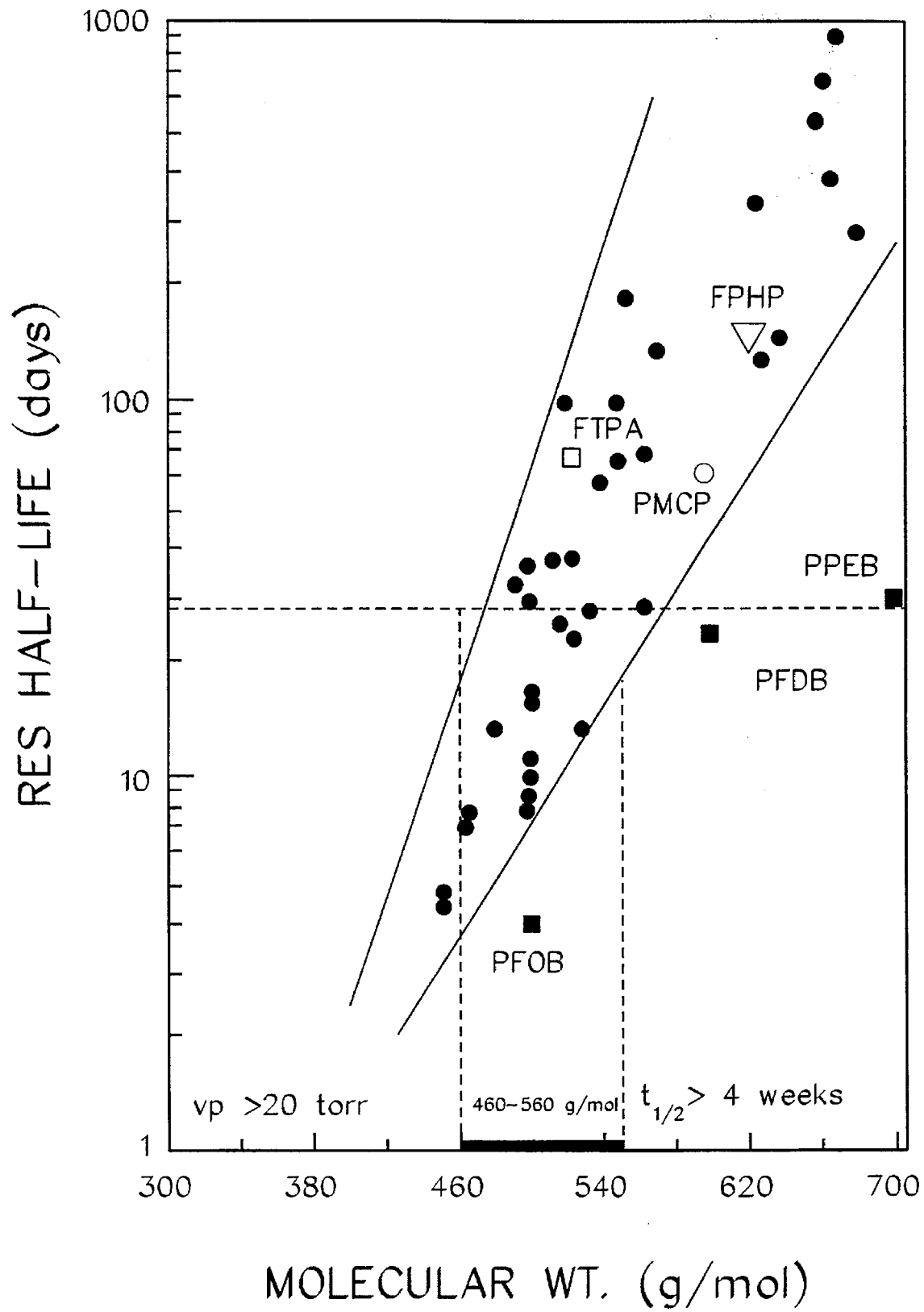
FIG. 4 is a plot illustrating the organ half-life in days vs. molecular weight of various fluorocarbons in g/mol. The plot includes a lower molecular weight cutoff which is related to the formation of gas emboli for fluorocarbons with vapor pressures greater than 20 torr. The plot also includes an upper molecular weight cutoff which is related to compounds having organ retention times of less than 4 weeks.
Figure 5:
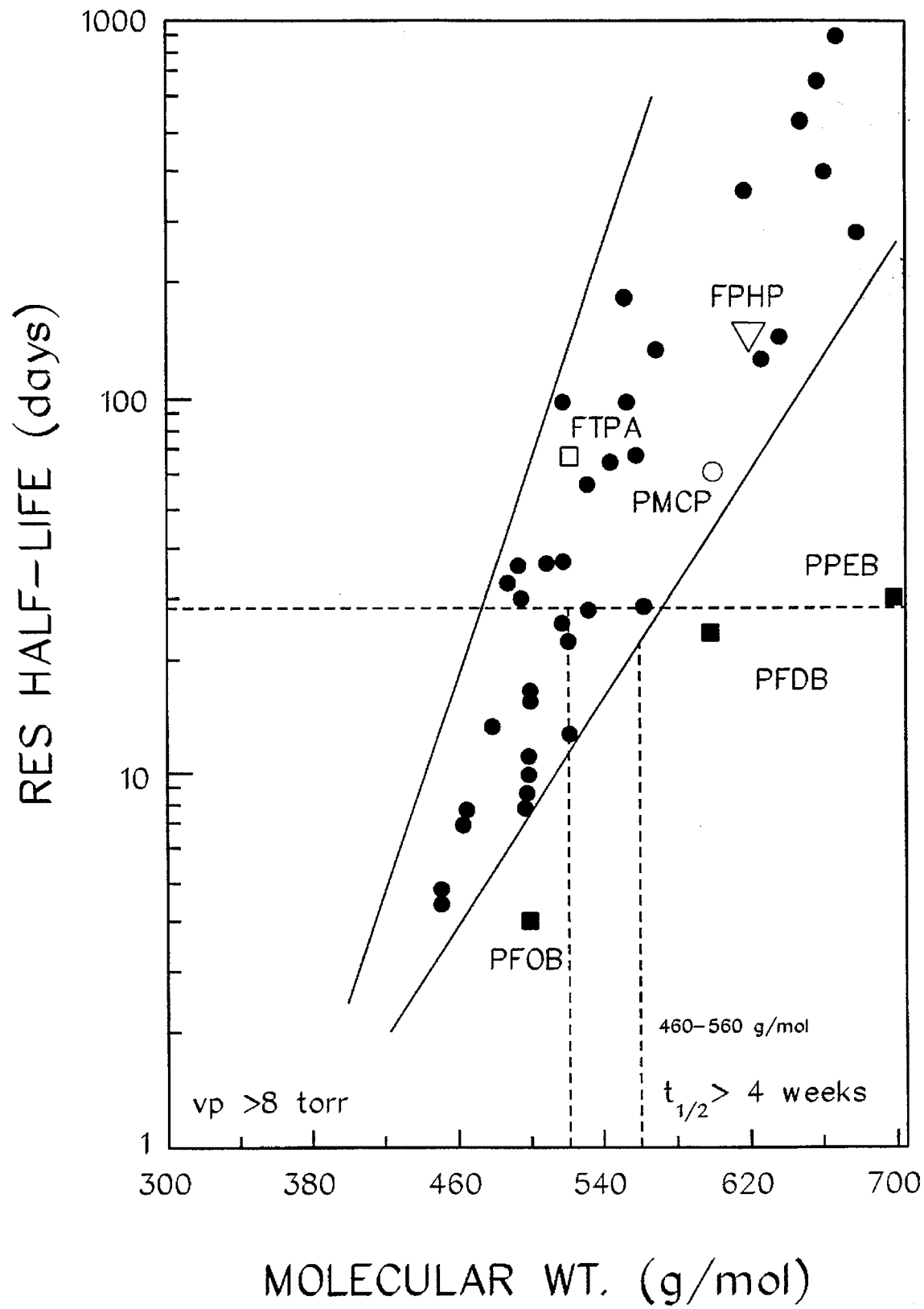
FIG. 5 is a plot illustrating the organ half-life in days vs. molecular weight of various fluorocarbons in g/mol. The plot includes a lower molecular weight cutoff of 520 g/mol to take into account pulmonary gas trapping (i.e. limit to less than 8 torr).

For single fluorocarbons, the fluorocarbon component must have a low vapor pressure and have a lipophilic moiety. Possible alternatives include those listed in Table I and FIG. 7, although other low vapor pressure, lipophilic fluorocarbons can be contemplated. FIGS. 4 and 5 illustrate the relationship between the molecular weight of various fluorocarbons and their half life time in days.

For mixtures of fluorocarbons, the first fluorocarbon may be selected from the list below. Such fluorocarbons must have a molecular weight of less than about 550 Daltons, and include bis(F-alkyl)ethenes such as $C_4F_9CH=CHC_4F_9$ ("F-44E"), i-$CF_3CF_9CH=CHC_6F_{13}$ ("F-i36E"), and cyclic fluorocarbons, such as $C_{10}F_{18}$ (F-decalin, perfluorodecalin or FDC); F-adamantane (FA); perfluoroindane; F-methyladamantane (FMA); F-1,3-dimethyladamantane (FDMA); perfluoro-2,2,4,4-tetramethylpentane; F-di- or F-tri-methylbicyclo[3,3,1]nonane (nonane); $C_{7-12}$ perfluorinated amines, such as F-tripropylamine, F-4-methyloctahydroquinolizine (FMOQ), F-N-methyl-decahydroisoquinoline (FMIQ), F-n-methyldecahydroquinoline (FHQ), and F-N-cyclohexylpyrrolidine (FCHP).

Other examples of appropriate first fluorocarbons include brominated perfluorocarbons, such as perfluorooctyl bromide ($C_8F_{17}Br$, USAN perflubron), 1-bromopentadecafluoroheptane ($C_7F_{15}Br$), and 1-bromotridecafluorohexane ($C_6F_{13}Br$, also known as perfluorohexyl bromide or PFHB). Other brominated fluorocarbons are disclosed in U.S. Pat. Nos. 3,975,512 and 4,987,154 to Long.

Also contemplated are first fluorocarbons having other nonfluorine substituents, such as 1-chloroheptadecafluorooctane ($C_8F_{17}Cl$, also referred to as perfluorooctyl chloride or PFOCl); perfluorooctyl hydride, and similar compounds having different numbers of carbon atoms.

Additional first fluorocarbons contemplated in accordance with this invention include perfluoroalkylated ethers, halogenated ethers (especially brominated ethers), or polyethers, such as $(CF_3)_2CFO(CF_2CF_2)_2OCF(CF_3)_2$; $(C_4F_9)_2O$. Further, fluorocarbon-hydrocarbon compounds may be used, such as, for example compounds having the general formula $C_nF_{2n+1}-C_{n'}H_{2n'+1}$; $C_nF_{2n+1}OC_{n'}H_{2n'+1}$; or $C_nF_{2n+1}CH=CHC_{n'}H_{2n'+1}$, wherein n and n' are the same or different and are from about 1 to about 10 (so long as the compound is a liquid at room temperature). Such compounds, for example, include $C_8F_{17}C_2H_5$ and $C_6F_{13}CH=CHC_6H_{13}$.

Particularly preferred fluorocarbons for use as the first fluorocarbon include perfluoroamines, terminally substituted linear aliphatic perfluorocarbons having the general structure:

$C_nF_{2n+1}R$, wherein n is an integer from 6 to 8 and R comprises a lipophilic moiety selected from the group of Br, Cl, I, $CH_3$, or a saturated or unsaturated hydrocarbon of 2 or 3 carbon atoms, bis (F-alkyl) ethenes having the general structure:

$C_nF_{2n+1}$—CH=CH—$C_{n'}F_{2n'+1}$, wherein the sum of n and n' equals 6 to 10, and perfluoroethers having the general structure:

$C_nF_{2n+1}$—O—$C_{n'}F_{2n'+1}$, wherein the sum of n and n' equals 6 to 9.

In addition, fluorocarbons selected from the general groups of perfluorocycloalkanes or perfluoroalkylcycloalkanes, perfluoroalkyl saturated heterocyclic compounds, or perfluorotertiary amines may be suitably utilized as the first fluorocarbon. See generally Schweighart, U.S. Pat. No. 4,866,096.

It will be appreciated that esters, thioethers, and other variously modified mixed fluorocarbon-hydrocarbon compounds, including isomers, are also encompassed within the broad definition of fluorocarbon materials suitable for use as the first fluorocarbon of the present invention. Other suitable mixtures of fluorocarbons are also contemplated.

Additional fluorocarbons not listed here, but having the properties described in this disclosure that would lend themselves to therapeutic applications, are also contemplated. Such fluorocarbons may be commercially available or specially prepared. As will be appreciated by one skilled in the art, there exist a variety of methods for the preparation of fluorocarbons that are well known in the art. See for example, Schweighart, U.S. Pat. No. 4,895,876.

The second fluorocarbon is preferably an aliphatic fluorocarbon substituted with one or more lipophilic moieties and having a higher molecular weight and lower vapor pressure than the first fluorocarbon. Advantageously, the lipophilic moiety is a terminal substitution on the fluorocarbon molecule. Preferably, the molecular weight of the second fluorocarbon is greater than about 540 Daltons. Constraints on the upper limit of the molecular weight of the second fluorocarbon will generally be related to its organ retention time and its ability to be solubilized by the first fluorocarbon. Usually, the second fluorocarbon has a molecular weight less than about 700 Daltons.

Most preferred second fluorocarbons have boiling points greater than about 150° C. and water solubilities of less than about $1 \times 10^{-9}$ moles/liter.

Of course, as will be appreciated by one skilled in the art, many fluorocarbons substituted with different lipophilic groups could be suitably used as the second fluorocarbon in the present invention. Such fluorocarbons may include esters, thioethers, and various fluorocarbon-hydrocarbon compounds, including isomers. Mixtures of two or more fluorocarbons satisfying the criteria set forth herein are also encompassed within the broad definition of fluorocarbon materials suitable for use as the second fluorocarbon of the present invention. Fluorocarbons not listed here, but having the properties described in this disclosure that would lend themselves to therapeutic applications are additionally contemplated.

The lipophilic moiety is optimally selected from the group consisting of Br, Cl, I, $CH_3$, or a saturated or unsaturated hydrocarbon of 2 or 3 carbon atoms. Consequently, preferred second fluorocarbons may be selected from the group of terminally substituted perfluorocarbon halides as represented by the general formula:

$C_nF_{2n+1}X$ or $C_nF_{2n}X_2$, wherein n is 8 or greater, preferably 10 to 12, and X is a halide selected from the group consisting of Br, Cl, or I;

1-alkyl-perfluorocarbons or dialkylperfluorocarbons as represented by the general formula:

$C_nF_{2n+1}$—$(CH_2)_n$$CH_3$ wherein n is 8 or greater, preferably 10 to 12, and n' is 0 to 2;

1-alkenyl-perfluorocarbons as represented by the general formula:

$C_nF_{2n+1}$—$C_{n'}H_{(2n'-1)}$, wherein n is 10 or more, preferably 10 to 12, and n' is either 2 or 3; or brominated linear or branched perfluoroethers or polyethers having the following general structure:

Br—$(C_nF_{2n+1}$—O—$C_{n'}F_{2n'+1})$, wherein n and n' are each at least 2 and the sum of n and n' is greater than or equal to 8.

Most preferably, the second fluorocarbon of the present invention is selected from the group consisting of linear or branched brominated perfluorinated alkyl ethers, perfluorodecyl bromide ($C_{10}F_{21}Br$); perfluorododecyl bromide ($C_{12}F_{25}Br$); 1-perfluorodecylethene ($C_{10}F_{21}CH=CH_2$); and 1-perfluorodecylethane ($C_{10}F_{21}CH_2CH_3$); with perfluorodecyl bromide particularly preferred.

In accordance with a first alternative definition, whether or not they satisfy the foregoing definitions, fluorocarbons having critical solution temperatures (CSTs) vs hexane more than 10° C. below the CST of a fluorocarbon having substantially the same molecular weight (variations of up to about 10 daltons being acceptable) are also suitable for use in the present invention. A comparison between the CST and molecular weight of a number of perfluorocarbons is presented in Table I. Methodology for determining CST is presented in Example 2.

Specifically, it has been found that a mixture of F-octyl bromide and F-decyl bromide satisfies the above stated requirements. In particular, a fluorocarbon phase which includes at least 10% wt/v of F-decyl bromide is preferred. Most preferably, the fluorocarbon phase includes F-octyl bromide at about 45% to 80% or 90% wt/v, and the F-decyl bromide is present in the fluorocarbon phase at about 10 to 55% wt/v.

TABLE I

Physical Properties of Minor Components Discussed in Literature
(Proposed Minor Components are listed in Boldface)

| Name | Formula | MW (g/mol) | b.p. (°C.) | CST (°C.) | $t_{1/2}$ (days) |
|---|---|---|---|---|---|
| Davis, et al. (U.S. Pat. No. 4,859,363) | | | | | |
| F-perhydrofluorene | $C_{13}F_{22}$ | 574 | 192–193 | n.a. | n.a. |
| F-perhydrophenanthrene | $C_{14}F_{24}$ | 624 | 215–216 | 48 | n.a. |
| F-perhydrofluoranthene | $C_{16}F_{26}$ | 686 | 242–243 | n.a. | n.a. |

TABLE I-continued

Physical Properties of Minor Components Discussed in Literature
(Proposed Minor Components are listed in Boldface)

| Name | Formula | MW (g/mol) | b.p. (°C.) | CST (°C.) | $t_{1/2}$ (days) |
|---|---|---|---|---|---|
| Kabalnov, et al. (Kolloidin Zh. 48:27–32(1986)) | | | | | |
| F-N-methylcyclohexylpiperidine | $C_{12}F_{21}N$ | 557 | | n.a. | 4060 |
| Meinert (U.S. Pat. No. 5,120,731); note these values are calculated, not measured. | | | | | |
| F-N-Cyclohexylmorpholine | $C_{10}F_{18}NO$ | 492 | n.a. | 31 | 13 |
| F-dimorpholinoethane | $C_{10}F_{20}N_2O_2$ | 560 | 164 | 38 | 24 |
| F-dimorpholinopropane | $C_{11}F_{22}N_2O_2$ | 610 | 182 | 45 | 50 |
| F-dimorpholinopentane | $C_{13}F_{26}N_2O_2$ | 710 | 215 | 60 | 280 |
| F-dipiperidine | $C_{10}F_{16}N_2$ | 452 | 145–150 | 36 | 24 |
| F-dipiperidinomethane | $C_{11}F_{18}N_2$ | 502 | 165–175 | 42 | 55 |
| F-dipiperidinoethane | $C_{12}F_{20}N_2$ | 552 | 181–186 | 49 | 124 |
| F-dipiperidinopropane | $C_{13}F_{22}N_2$ | 602 | 195–203 | 56 | 282 |
| F-dipiperidinobutane | $C_{14}F_{24}N_2$ | 652 | 231–238 | 72 | 1460 |
| Present Invention | | | | | |
| F-decalin | $C_{10}F_{18}$ | 462 | 142 | 22 | 7 |
| F-hexyl bromide | $C_6F_{13}Br$ | 399 | n.a. | n.a. | 2 |
| F-octyl bromide | $C_8F_{17}Br$ | 499 | 143 | (−19)[a] | 4 |
| F-decyl bromide | $C_{10}F_{21}Br$ | 599 | (198)[b] | (<0)[a] | 23 |
| F-bromopolyether | $C_{11}F_{23}O_3Br$ | 697 | n.a. | 32 | 30 |

[a] values for the critical solution temperature with hexane are estimated from extrapolation of linear plots of the critical solution temperature vs. hydrocarbon chain length.
[b] the value of the boiling point of F-decylbromide is estimated from Hildebrand solution theory.

B. The Emulsifying Agent

The fluorocarbon emulsion also includes an emulsifying agent. As used in this specification, an emulsifying agent is any compound or composition that aids in the formation and maintenance of the droplets of the discontinuous phase by forming a layer at the interface between the discontinuous and continuous phases. The emulsifying agent may comprise a single compound or any combination of compounds, such as in the case of co-surfactants.

In the present invention, preferred emulsifying agents are selected from the group consisting of phospholipids, nonionic surfactants, fluorinated surfactants, which can be neutral or anionic, and combinations of such emulsifying agents.

Lecithin is a phospholipid that has frequently been used as a fluorocarbon emulsifying agent, as is more fully described in U.S. Pat. No. 4,865,836. Egg yolk phospholipids have shown great promise as emulsifying agents for fluorocarbons. See e.g., Long, U.S. Pat. No. 4,987,154.

Other emulsifying agents may be used with good effect, such as fluorinated surfactants, also known as fluorosurfactants. Fluorosurfactants that can provide stable emulsions include triperfluoroalkylcholate; perfluoroalkylcholestanol; perfluoroalkyloxymethylcholate; $C_3F_7O(CF_2)_3C(=O)NH(CH_2)_3N(O)(CH_3)_2$ (XMO-10); and fluorinated polyhydroxylated surfactants, such as, for example, those discussed in "Design, Synthesis and Evaluation of Fluorocarbons and Surfactants for In Vivo Applications New Perfluoroalkylated Polyhydroxylated Surfactants" by J. G. Riess, et al., Biomat. Artif. Cells Artif. Organs 16: 421–430 (1988).

The nonionic surfactants suitable for use in the present invention include polyoxyethylene-polyoxypropylene copolymers. An example of such class of compounds is Pluronic, such as Pluronic F-68. Artionic surfactants, particularly fatty acids (or their salts) having 12 to 24 carbon atoms, may also be used. One example of a suitable anionic surfactant is oleic acid, or its salt, sodium oleate.

It will be appreciated that choice of a particular emulsifying agent is not central to the present invention. Indeed, virtually any emulsifying agent (including those still to be developed) capable of facilitating formation of a fluorocarbon-in-water emulsion can form improved emulsions when used in the present invention. The optimum emulsifying agent or combination of emulsifying agents for a given application may be determined through empirical studies that do not require undue experimentation. Consequently, one practicing the art of the present invention should choose the emulsifying agent or combination of emulsifying agents for such properties as biocompatibility.

C. The Continuous Phase

The continuous phase comprises an aqueous medium. Preferably, the medium is physiologically acceptable. For instance, a preferred emulsion will have the ability to buffer and maintain pH, as well as provide an appropriate osmolality. This typically has been achieved in the art through the inclusion in the aqueous phase of one or more conventional buffering and/or osmotic agents, or an agent that combines these properties.

Additionally, one may supplement the continuous phase with other agents or adjuvants for stabilizing or otherwise increasing the beneficial aspects of the emulsion. These agents or adjuvants include: cholesterol, tocopherols, and/or mixtures or combinations thereof.

D. Preparation of the Emulsion

Fluorocarbon emulsions according to the invention are prepared by means of conventional emulsification procedures, such as, for example, mechanical or ultrasonic emulsification of an emulsion formulation in a Manton-Gaulin mixer or Microfluidizer (Microfluidics Corp., Newton, Mass.) as described in Example 1.

The single fluorocarbon, or the first and second fluorocarbons, are combined with the aqueous phase in the desired ratios, together with the surfactant. Usually, a pre-emulsion mixture is prepared by simple mixing or blending of the various components. This pre-emulsion is then emulsified in the desired emulsification apparatus.

When a composition of fluorocarbons is used, the second fluorocarbon can comprise from about 0.1% to 50% (w/w)

of the total amount of fluorocarbon; in preferred embodiments, the second fluorocarbon comprises from about 0.5% to about 40% (w/w) of the total amount of fluorocarbon, with the first fluorocarbon comprising the remainder of the total fluorocarbon. The combined fluorocarbon concentration in the emulsion is preferably anywhere within the range of about 20% to about 125% (w/v). In preferred emulsions, the total perfluorocarbon concentration is from about 30%, 40%, or 50% to about 70%, 80%, 90%, or 100% (w/v). Emulsifiers are added in concentrations of from about 0.1% to 10%, more preferably 1% or 2% to about 6% (w/v).

EXAMPLE 1

Preparation of Reference Emulsion Composition of Reference Emulsion: Perflubron/Lecithin (90/4% w/v)

A reference emulsion containing 90 g PFOB, 4 g egg yolk phospholipid (EYP), and physiological levels of salts and buffers was prepared by high pressure homogenization according to the method of Long (U.S. Pat. No. 4,987,154).

EXAMPLE 2

Measurement of Critical Solution Temperature (CST)

Critical solution temperature for fluorocarbon liquids was measured in the following manner: Equivolume mixtures of the test fluorocarbon and hydrocarbon (e.g., hexane) are placed in a sealed vial and submerged in a temperature controlled water bath. Samples are cooled until two distinct phases are present. At this point, the temperature is increased slowly. The lowest temperature at which the two phases are completely miscible (i.e., a single liquid phase) is defined as the CST.

For comparison purposes, all CST temperatures used in this patent are reported versus hexane. It is often not possible, however, to measure the CST for lipophilic fluorocarbons versus hexane, since the CSTs for these substances are very low. Thus, the CST for lipophilic substances is often measured in longer chain length hydrocarbons, and the value versus hexane is determined via extrapolation of linear plots of CST vs. alkane chain length.

Further, several other second fluorocarbons are considered similary acceptable. In particular, it appears that perfluorobromoethers, perfluorooctylethane (PFOE), perfluorononyl bromide, perfluorooctyl ethane, and other compounds selected from the group of alkyl-perfluoro-alkanes (such as $C_8F_{17}C_2H_5$ and $C_{10}F_{21}C_2F_5$) either individually or in mixtures, are believed suitable.

In any case, the second fluorocarbon is chosen such that when mixed with the first fluorocarbon in appropriate ratios, it eliminates pulmonary gas trapping (i.e. the fluorocarbon phase has a vapor pressure of less than 20 torr, and preferably less than 8 torr, and has an organ half-life of about 3 to 4 weeks. It is possible to derive acceptable compositions through calculation of the vapor pressure of the mixture of fluorocarbons with Raoult's law, as was done in FIG. 6, or by determining the vapor pressure empirically.

EXAMPLE 3

Effect of Vapor Pressure on IPRV

Figure 6:
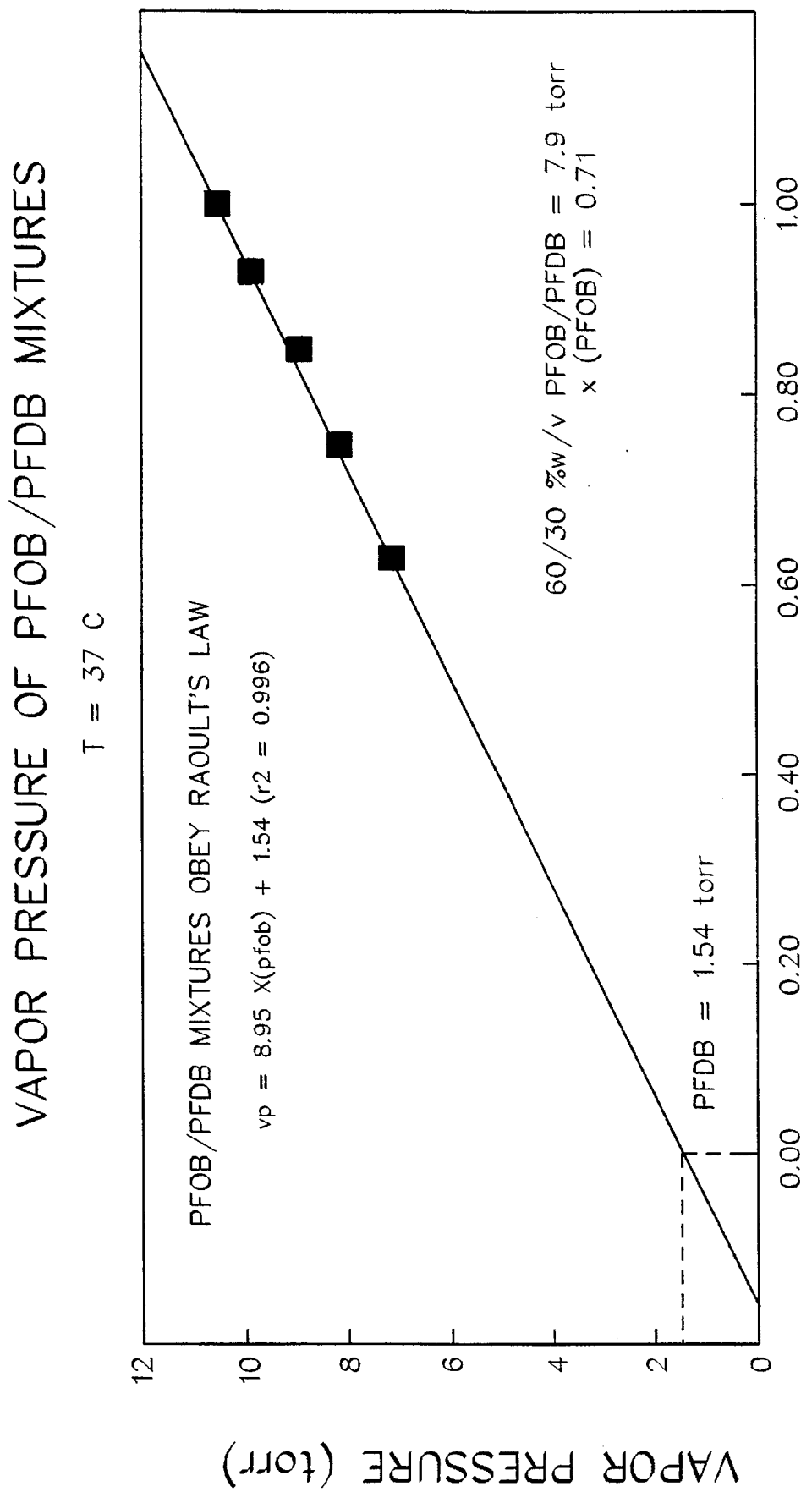
FIG. 6 is a graph of fluorocarbon vapor pressure in torr at 37 degrees celsius for various mole fractions in mixtures of perfluorooctyl bromide (PFOB) and perfluorodecyl bromide (PFDB).

FIGS. 1 and 2 illustrate the effect of vapor pressure on IPRV in rats and rabbits respectively. It is clear that at vapor pressures less than about 8 torr IPRV is substantially reduced. Further, as illustrated in FIG. 6, mixtures of 60% w/v PFOB and 30% w/v PFDB obey Raoult's law and have a vapor pressure of about 8 torr. These mixtures are able to effectively decrease IPRV to levels observed for single fluorocarbons with vapor pressures of about 0.1 torr.

Although the present invention has been disclosed in the context of certain preferred embodiments, it is intended that the scope of the invention be measured by the claims that follow, and not be limited to those preferred embodiments.

We claim:

1. A fluorocarbon emulsion exhibiting reduced pulmonary gas-trapping properties, comprising:

an aqueous phase;

an emulsifying agent; and a liquid fluorocarbon phase comprising a mixture of at least two fluorocarbons in a weight ratio of from about 20:1 to about 1:20 wherein at least one fluorocarbon has a covalently attached lipophilic moiety consisting of Br, Cl or I saturated or unsaturated hydrocarbon chain of 2 or 3 carbon atoms, said mixture having a vapor pressure of less than about 20 Torr at 37° C., and having an organ half-life of less than about 6 weeks.

2. The fluorocarbon emulsion of claim 1, wherein said fluorocarbon phase comprises a first fluorocarbon having an organ half-life of less than about 4 weeks, and a second fluorocarbon having a vapor pressure less than said first fluorocarbon.

3. The fluorocarbon emulsion of claim 2, wherein said first fluorocarbon has a molecular weight of about 460 to 550 Daltons, and said second fluorocarbon has a molecular weight of about 560 to 700 Daltons.

4. The fluorocarbon emulsion of claim 1, wherein said fluorocarbon phase has a vapor pressure at 37° C. of less than about 10 torr.

5. The fluorocarbon emulsion of claim 1, wherein said fluorocarbon phase has a vapor pressure at 37° C. of less than 8 torr.

6. A fluorocarbon emulsion exhibiting reduced pulmonary gas-trapping properties, comprising:

an aqueous phase;

an emulsifier; and a fluorocarbon phase including at least 10% weight by volume of F-decyl bromide.

7. The fluorocarbon emulsion of claim 6, wherein said fluorocarbon phase additionally comprises F-octyl bromide.

8. The fluorocarbon emulsion of claim 7, wherein said F-octyl bromide is present in said fluorocarbon phase at about 45% to 90% weight per volume, and said F-decyl bromide is present in said fluorocarbon phase at about 10% to 55% weight per volume.

9. In a method of preparing a fluorocarbon emulsion for intravenous administration to a patient, by forming an emulsion of an aqueous phase, an emulsifier, and a first fluorocarbon in a fluorocarbon phase wherein the vapor pressure of the fluorocarbon phase is greater than about 8 Torr at 37° C., the improvement comprising:

reducing the pulmonary gas trapping effect of the emulsion upon intravenous administration by providing in combination with the first fluorocarbon in the fluorocarbon phase an effective amount of a second fluorocarbon comprising a covalently attached lipophilic moiety selected from the group consisting of Br, Cl or I, wherein the addition of the second fluorocarbon reduces the vapor pressure of the fluorocarbon phase at 37° C. to less than about 8 Torr and wherein the fluorocarbon phase has a melting point less than about 37° C. and an organ retention half-life less than about 4 weeks.

10. The method of claim 9, wherein said second fluorocarbon is a bromofluorocarbon.

11. The method of claim 9, wherein said fluorocarbon phase comprises from about 50% to about 99.9% w/w of said first fluorocarbon and from about 0.1% to about 50% w/w of said second fluorocarbon.

12. The method of claim 9 wherein said second fluorocarbon has a molecular weight in the range from about 540 Daltons to about 700 Daltons.

13. In a method for administering a fluorocarbon emulsion to a mammal, wherein the emulsion comprises an aqueous phase, an emulsifier, and a first fluorocarbon in a fluorocarbon phase wherein the vapor pressure of the fluorocarbon phase is greater than about 8 Torr at 37° C., the improvement comprising:

reducing the pulmonary gas trapping effect of the emulsion upon intravenous administration by providing in combination with the first fluorocarbon in the fluorocarbon phase an effective amount of a second fluorocarbon comprising a covalently attached lipophilic moiety selected from the group consisting of Br, Cl or I, wherein the addition of the second fluorocarbon reduces the vapor pressure of the fluorocarbon phase at 37° C. to less than about 8 Torr and wherein the fluorocarbon phase has a melting point less than about 37° C. and an organ retention half-life less than about 4 weeks.

14. The method of claim 13, wherein said fluorocarbon phase comprises from about 50% to about 99.9% w/w of said first fluorocarbon and from about 0.1% to about 50% w/w of said second fluorocarbon.

15. The method of claim 13 wherein said second fluorocarbon has a molecular weight in the range from about 540 Daltons to about 700 Daltons.

* * * * *

UNITED STATES PATENT AND TRADEMARK OFFICE
CERTIFICATE OF CORRECTION

PATENT NO. : 5,635,538
DATED : June 3, 1997
INVENTOR(S) : Weers, et al.

It is certified that error appears in the above-identified patent and that said Letters Patent is hereby corrected as shown below:

On cover page, at [*], under "Notice", Pat. No. 5,608,930 should read -- 5,628,930 --

Signed and Sealed this

Twenty-fourth Day of March, 1998

Attest:

BRUCE LEHMAN

Attesting Officer     *Commissioner of Patents and Trademarks*